United States Patent [19]  
Vignali et al.

[11] Patent Number: 4,923,992  
[45] Date of Patent: May 8, 1990

[54] PROCESS FOR THE PREPARATION OF BIS(2,2,6,6-TETRAMETHYL-4-PIPERIDYL)AMINE

[75] Inventors: Graziano Vignali, Sasso Marconi; Giovanni De Roit, Bologna, both of Italy; Paul Dubs, Marly; Peter Baumeister, Flüh, both of Switzerland

[73] Assignee: Ciba-Geigy Corporation, Ardsley, N.Y.

[21] Appl. No.: 329,168

[22] Filed: Mar. 27, 1989

[30] Foreign Application Priority Data

Apr. 7, 1988 [IT] Italy ............................... 20117 A/88

[51] Int. Cl.$^5$ ............................................. C07D 401/12
[52] U.S. Cl. ................................................... 546/186
[58] Field of Search ............................................ 546/186

[56] References Cited

U.S. PATENT DOCUMENTS

| | | | |
|---|---|---|---|
| 3,684,765 | 8/1972 | Matsui et al. | 546/186 |
| 3,904,581 | 9/1975 | Murayama et al. | 546/186 |
| 4,369,321 | 1/1983 | Cantatore | 546/188 |
| 4,526,971 | 7/1985 | Disteldorf et al. | 546/186 |
| 4,533,688 | 8/1985 | Yoda et al. | 544/212 |
| 4,605,743 | 8/1986 | Malz, Jr. et al. | 346/186 |

FOREIGN PATENT DOCUMENTS

| | | | |
|---|---|---|---|
| 0022079 | 1/1984 | European Pat. Off. | 546/190 |
| 0155909 | 9/1985 | European Pat. Off. | 546/22 |
| 0209126 | 1/1987 | European Pat. Off. | 544/212 |
| 0209127 | 1/1987 | European Pat. Off. | 544/212 |
| 3321332 | 12/1984 | Fed. Rep. of Germany | 546/186 |

OTHER PUBLICATIONS

Methoden der Organischen Chemie, Houben–Weyl, 4th Ed., vol. IV/1c, pp. 440–442, (1980).

Primary Examiner—Robert T. Bond  
Attorney, Agent, or Firm—JoAnn Villamizar

[57] ABSTRACT

A one step process for the preparation of bis(2,2,6,6-tetramethyl-4-piperidyl)amine by reacting 2,2,6,6-tetramethyl-4-piperidone or 2,2,6,6-tetramethyl-4-piperidone x $H_2O$ with ammonia and hydrogen in the presence of a hydrogenation catalyst, characterized in that the molar ratio of 2,2,6,6-tetramethyl-4-piperidone versus ammonia is between 1:0.4 and 1:0.8.

16 Claims, No Drawings

PROCESS FOR THE PREPARATION OF BIS(2,2,6,6-TETRAMETHYL-4-PIPERIDYL)AMINE

The present invention relates to an improved process for the preparation of bis(2,2,6,6-tetramethyl-4-piperidyl)amine.

Bis(2,2,6,6-tetramethyl-4-piperidyl)amine is an intermediate for the preparation of numerous light stabilizers. It is known that synthetic polymers undergo more or less severe chemical and physical changes when they are subjected to the action of sunlight or other sources of ultraviolet radiation. To retard the deleterious effect of ultraviolet radiations on synthetic polymers, suitable light stabilizers, e.g. those described in EP-A-22,079, EP-A-155,909, EP-A-209,126, EP-A-209,127, US-A-3,684,765, US-A-3,904,581, US-A-4,369,321 and US-A-4,533,688, are usually added to the polymers.

Several methods have been proposed for the preparation of bis(2,2,6,6-tetramethyl-4-piperidyl)amine. For example, in US-A-4,533,688 the preparation of bis(2,2,6,6-tetramethyl-4-piperidyl)amine by hydrogenation of a mixture of 2,2,6,6-tetramethyl-4-piperidone and ammonium chloride in the presence of platinum oxide is disclosed. US-A-3,684,765 generally discloses the formation of bis(2,2,6,6-tetramethyl-4-piperidyl)amine which is obtained by reductive amination of 2,2,6,6-tetramethyl-4-piperidone with ammonia, but no information is given about the reaction conditions and the results obtained.

The present invention pertains to an improved one step process for the preparation of bis(2,2,6,6-tetramethyl-4-piperidyl)amine by reacting 2,2,6,6-tetramethyl-4-piperidone or 2,2,6,6-tetramethyl-4-piperidone$\times H_2O$ with ammonia and hydrogen in the presence of a nobel metal hydrogenation catalyst, characterized in that the molar ratio of 2,2,6,6-tetramethyl-4-piperidone versus ammonia is between 1:0.4 and 1:0.8, preferably 1:0.48 and 1:0.8.

The possibility of carrying out the reaction under moderate temperatures and pressures, the high yields of product and the low cost of starting materials make the present invention advantageous and suitable for industrial use.

The molar ratio of 2,2,6,6-tetramethyl-4-piperidone versus ammonia is preferably between 1:0.5 and 1:0.7, in particular between 1:0.52 and 1:0.7, for example between 1:0.54 and 1:0.6.

The nobel metal hydrogenation catalyst which may optionally be supported on a suitable inert material is for example platinum or plalladium, or a mixture of platinum and palladium or of platinum and rhodium. Platinum is preferred.

The reductive amination according to the present invention can be carried out in the presence or without an organic or inorganic acid. When the reaction is carried out in the presence of an organic or inorganic acid as co-catalyst (pk$_a$-value: 1–5.5, preferably 4–5), suitable acids are e.g. acetic acid, propionic acid, p-toluenesulfonic acid, benzoic acid, 2-chlorobenzoic acid, 2-phenylbenzoic acid, toluic acid, hexahydrobenzoic acid, sulfuric acid and phosphoric acid. Benzoic acid, toluic acid, hexahydrobenzoic acid and sulfuric acid are preferred. The above mentioned acids can also be used in the form of their ammonium salts. The organic or inorganic acid is conveniently present in an amount of 0.001 to 0.1 mole, preferably 0.001 to 0.05 mole, in particular 0.002 to 0.01 mole, per mole of 2,2,6,6-tetramethyl-4-piperidone.

When an organic or inorganic acid is used as co-catalyst, it is convenient to neutralize the reaction mixture after the end of the reaction. Preferred bases are inorganic bases, in particular the hydroxide or carbonate of sodium or potassium, which are preferably used in a quantity at least equivalent to the acid.

The reductive amination according to the present invention can be carried out without any solvent or in the presence of an inert solvent, e.g. water, lower alcohols such as methanol, ethanol or isopropanol, mixtures of water and lower alcohols, hydrocarbons such as toluene, xylene or cyclohexane. Preferred solvents are methanol, ethanol and isopropanol, in particular methanol.

The instant process is preferably carried out at a temperature of 20° to 120° C., especially 30° to 100° C.

The hydrogen pressure is for example 1 to 100 bar, in particular 5 to 80 bar.

The present process is conveniently carried out in an autoclave which is charged with the starting materials, the catalysts and optionally with a solvent. The reaction mixture is heated and stirred under constant hydrogen pressure to the completion of the hydrogen uptake. Alternatively, in a variation of the instant process one of the starting materials can be added continuously to the reaction mixture.

The ammonia needed may be used in gaseous form as well as in form of an aqueous solution or an alcoholic solution.

The reaction time depends on different facts such as temperature, pressure, stirring speed, amount of hydrogenation catalyst etc.; for example, in the presence of acids as co-catalysts the reaction proceeds more quickly.

The kind and the amount of by-products which are formed during the reaction depend on the molar ratio of the starting materials 2,2,6,6-tetramethyl-4-piperidone and ammonia and, in particular, on the presence and on the kind of acid used as co-catalyst. Possible by-products are e.g. 4-amino-2,2,6,6-tetramethylpiperidine, 4-hydroxy-2,2,6,6-tetramethylpiperidine and 4-isopropylamino-2,2,6,6-tetramethylpiperidine. In the presence of acids lower amounts of 4-hydroxy-2,2,6,6-tetramethylpiperidine are formed, whereas in the absence of acids, lower amounts of 4-isopropylamino-2,2,6,6-tetramethylpiperidine and different not identified products are formed.

The reaction is preferably carried out in the presence of a co-catalyst, when the molar ratio of 2,2,6,6-tetramethyl-4-piperidone versus ammonia is between 1:0.48 and 1:0.6.

4-Amino-2,2,6,6-tetramethylpiperidine which is the main by-product of the reaction can be recycled, if desired, that means, the 4-amino-2,2,6,6-tetramethylpiperidine obtained can be added to a new reaction mixture. After recycling, the yield of bis(2,2,6,6-tetramethyl-4-piperidyl)amine is normally over 90% of theory.

Therefore, a process wherein the by-product 4-amino-2,2,6,6-tetramethylpiperidine obtained during the preceding preparation is added to the new reaction mixture is preferred.

Bis(2,2,6,6-tetramethyl-4-piperidyl)amine can be isolated from the reaction mixture by known processes, for example by fractional distillation or by distillation of the volatile products and subsequent recrystallization of the residue. It is also possible to use the residue directly after distillation of the volatile products.

All starting materials are known and commercially available; if desired, they can also be prepared by analogy to known methods.

The following examples illustrate the present invention.

EXAMPLE 1

An autoclave (1 liter) is charged with 388.1 g (2.5 mol) of 2,2,6,6-tetramethyl-4-piperidone, 100 ml of methanol, 2.5 g (0.02 mol) of benzoic acid, 23.33 g (1.37 mol) of gaseous ammonia and 4.5 g of 5% Pt on carbon. The reaction is carried out under a hydrogen pressure of 50 bar at a temperature of 60° C., until complete absorption (about 8 hours). Subsequently, the catalyst is removed by filtration and the solvent is evaporated by distillation. The residue is separated by fractional distillation in the presence of 1 g of sodium hydroxide to give 63.2 g of distillate (boiling point: ~80° C./2.7 mbar) containing 79% of 4-amino-2,2,6,6-tetramethylpiperidine, and 301.4 g of bis(2,2,6,6-tetramethyl-4-piperidyl)amine as residue (boiling point: ~120° C./0.5 mbar; yield: 81.6%).

EXAMPLE 2

The general procedure described in Example 1 is repeated, but the 63.2 g of distillate containing 4-amino-2,2,6,6-tetramethylpiperidine obtained in Example 1 are additionally added to the reaction mixture.

Subsequently, the same procedure is repeated three times. Each time, the distillate containing 4-amino-2,2,6,6-tetramethylpiperidine obtained during the preceding preparation is added to the new reaction mixture.

Yield of bis(2,2,6,6-tetramethyl-4-piperidyl)amine

Calculated: 1477.5 g;

Obtained: 1396.8 g (=94.5% of theory).

EXAMPLES 3–9

Following the general procedure described in Example 1 and using 2.5 moles of 2,2,6,6-tetramethyl-4-piperidone (TAA) and the reagents and solvents indicated in Table 1, bis(2,2,6,6-tetramethyl-4-piperidyl)amine is prepared.

TABLE 1

| Example | Molar ratio of TAA/NH$_3$ | Co-catalyst (mol/mol TAA) | Solvent (100 ml) | Yield of bis(2,2,6,6-tetramethyl-4-piperidyl)amine[1] |
|---|---|---|---|---|
| 3 | 1/0.54 | — | CH$_3$OH | 82.9% |
| 4 | 1/0.49 | benzoic acid (0.008) | CH$_3$OH | 84.5% |
| 5 | 1/0.55 | benzoic acid (0.008) | — | 79.2% |
| 6 | 1/0.55 | benzoic acid (0.008) | CH$_3$OH | 79.6% |
| 7 | 1/0.57 | hexahydrobenzoic acid (0.004) | CH$_3$OH | 80.1% |
| 8 | 1/0.55 | p-toluic acid (0.008) | CH$_3$OH | 82.3% |
| 9 | 1/0.56 | H$_2$SO$_4$ (0.008) | CH$_3$OH | 84.6% |

[1]determined by Gas Liquid Chromatography (GLC).

We claim:

1. A one step process for the preparation of bis(2,2,6,6-tetramethyl-4-piperidyl)amine by reacting 2,2,6,6-tetramethyl-4-piperidone or 2,2,6,6-tetramethyl-4-piperidone×H$_2$O with ammonia and hydrogen in the presence of a nobel metal hydrogenation catalyst, characterized in that the molar ratio of 2,2,6,6-tetramethyl-4-piperidone versus ammonia is between 1:0.4 and 1:0.8.

2. A process according to claim 1, wherein the reaction is carried out in the presence of a co-catalyst, when the molar ratio of 2,2,6,6-tetramethyl-4-piperidone versus ammonia is between 1:0.48 and 1:0.6.

3. A process according to claim 1, wherein the molar ratio of 2,2,6,6-tetramethyl-4-piperidone versus ammonia is between 1:0.5 and 1:0.7.

4. A process according to claim 1, wherein the molar ratio of 2,2,6,6-tetramethyl-4-piperidone versus ammonia is between 1:0.52 and 1:0.7.

5. A process according to claim 1, wherein the nobel metal hydrogenation catalyst is platinum or palladium.

6. A process according to claim 1, which is carried out in the presence of an organic or inorganic acid as co-catalyst.

7. A process according to claim 6, wherein the co-catalyst is present in an amount between 0.001 and 0.1 mole per mole of 2,2,6,6-tetramethyl-4-piperidone.

8. A process according to claim 6, wherein the co-catalyst is present in an amount between 0.001 and 0.05 moles per mole of 2,2,6,6-tetramethyl-4-piperidone.

9. A process according to claim 6, wherein the co-catalyst is present in an amount between 0.002 and 0.01 mole per mole of 2,2,6,6-tetramethyl-4-piperidone.

10. A process according to claim 6, wherein the co-catalyst is benzoic acid, toluic acid, hexahydrobenzoic acid or sulfuric acid.

11. A process according to claim 1, which is carried out without any solvent.

12. A process according to claim 1, which is carried out in an inert solvent.

13. A process according to claim 12, wherein the solvent is methanol, ethanol or isopropanol.

14. A process according to claim 1, which is carried out at a temperature of 20° to 120° C.

15. A process according to claim 1, which is carried out at a hydrogen pressure of 1 to 100 bar.

16. A process according to claim 1, wherein the by-product 4-amino-2,2,6,6-tetramethylpiperidine obtained during the reaction is recycled as starting material in a new reaction process.

* * * * *